United States Patent [19]

Poulle et al.

[11] Patent Number: 5,681,750
[45] Date of Patent: Oct. 28, 1997

[54] PROCESS FOR PREPARING A C1-ESTERASE INHIBITOR CONCENTRATE (C1-INH), AND CONCENTRATE OBTAINED, FOR THERAPEUTIC USE

[75] Inventors: Michel Poulle; Miryana Burnouf (nee Radosevich), both of Wavrin, France

[73] Assignee: Association pour l'Essor de la Transfusion Sanguine dans, Lille, France

[21] Appl. No.: 508,559

[22] Filed: Jul. 28, 1995

[30] Foreign Application Priority Data

Jul. 28, 1994 [FR] France .................... 94 09353

[51] Int. Cl.$^6$ .................. G01N 33/00; G01N 1/00; G01N 1/18; C12N 9/96
[52] U.S. Cl. .................. 436/86; 436/825; 436/821; 436/178; 436/175; 435/2; 435/188
[58] Field of Search ............... 435/2, 189, 188; 436/86, 63, 174, 175, 178, 177, 501, 821, 825, 826

[56] References Cited

U.S. PATENT DOCUMENTS 5,030,578  7/1991  Pilatte et al. .................. 436/86

OTHER PUBLICATIONS

McKay et al. Mol. Immunol. vol. 18, 1981, pp. 349–357 Abstract Attached.
Harrison, R. Biochemistry, vol. 22, 1983, pp. 5001–5007.
Gadek et al. NEJ Med. vol. 302, pp. 542–546.
"Journal of Chromatography", 582 (1992) pp. 65–70 Müller.
"Journal of Chromatography", 510 (1990) pp. 133–140 Teh et al.

*Primary Examiner*—Blaine Lankford
*Assistant Examiner*—Christopher R. Tate
*Attorney, Agent, or Firm*—Birch, Stewart, Kolasch & Birch

[57] ABSTRACT

Disclosed is a process for preparing a C1-esterase inhibitor concentrate, of human plasma origin, comprising 2 separations by chromatography on ion exchanger gels of tentacular type.

21 Claims, No Drawings

PROCESS FOR PREPARING A C1-ESTERASE INHIBITOR CONCENTRATE (C1-INH), AND CONCENTRATE OBTAINED, FOR THERAPEUTIC USE

The present invention concerns a process for preparing a C1-esterase inhibitor concentrate from a human plasma fraction which comprises two chromatographic separation steps on anion exchanger then on cation exchanger gels, and two treatments for removal of possible viral contaminants. The obtained concentrate is intended for therapeutic use.

BACKGROUND OF THE INVENTION

C1-esterase inhibitor (known in abreviated form as C1-INH) is a protease inhibitor present in the plasma, which controls the activation of the first complement component, C1, and inactivates its sub-components C1r and C1s. It also inhibits other serine proteases of coagulation and fibrinolytic and contact systems, like kallikrein, plasmin-activated Hageman factor and factor XIa.

The C1-INH from human plasma consists of a single glycosylated polypeptide chain, with a molecular weight of 104 000 daltons.

Deficiencies in C1-INH are associated with more or less severe pathologies that may even be lethal. Patients suffering from hereditary angioedema suffer from a lack of C1-INH (type 1) or show a reduced C1-INH activity (type II). Another form (type III) of hereditary angioedema results from an abnormal binding of albumine to C1-INH. There are also acquired C1-INH deficiencies due to an abnormally high catabolism of the inhibitor or to the presence of auto-antibodies.

The disease appears as facial oedema, oedema on extremities, on intestinal walls and in the higher respiratory tract.

Different therapies are applied on prophylactic basis in order to reduce the severity of attacks, using antifibrinolytic agents or hormones, but they are not efficient against the acute crisis and, besides, they induce side effects that are incompatible with a long-term therapy. For acute crisis, treatments with kallikrein inhibitors, such as aprotinin, are applied but they can induce allergic reactions.

A C1-INH replacement therapy using fresh plasma has already been applied to high-risk patients undergoing oral surgery. This therapy has brought a remission of the disease symptoms. However, plasma brings an additional load of useless proteins, particularly complement constituents C2 and C4, which can aggravate the pathology.

Replacement therapy with purified C1-INH appears to be a treatment of choice for acute attacks, for long-term therapy or pre-operatory prophylaxis as well.

At present, several partially purified concentrates are available but all the described preparation processes are difficult to adapt on an industrial scale, due either to technical problems, or to costs of materials to be used:

Harrison (Biochemistry 1983; 22:5001–5007) reports a purification process that can be applied on laboratory scale with the purpose to characterize the molecule, but the duration of this process is too long for transposition on industrial scale;

Reboul et al. (Fed. Eur. Biochem. Soc. Lett. 1977; 79:45–50) and Pilatte et al. (J. Immunol. Methods 1989; 120:37–43) report preparation processes comprising an affinity chromatography on lectins;

Prograis et al. (J. Immunol. Methods 1987; 99:113–122) report a process comprising an affinity chromatography on gel chelated with zinc;

Alsenz et al. (J. Immunol. Methods 1987; 96:107–114) report a preparation process by immunoadsorption with a monoclonal antibody.

In all these processes, toxic stabilizers are added to the buffers in order to protect the C1-INH activity.

A first large scale preparation process was described by Vogelaar et al. (Vox Sang. 1974; 26:118–127) by batch adsorption on DEAE-Sephadex® and elution with high salt concentration, then precipitation with ammonium sulfate in order to eliminate albumin and ceruloplasmin.

The process was improved (Wickerhauser. Joint Meet. 18th Congr. ISH/16th Congr. ISBT, Montreal 1980, Abst: 161 and Gadek et al. New Eng. J. Med. 1980; 302:542–546) by combining two batchwise chromatographic steps, on DEAE-Sephadex®, then on CM-Sephadex®, and a precipitation step with PEG, the final product being of "intermediate purity".

Finally, a "high purity" product was obtained by adding a final precipitation step in the presence of salts (Wickerhauser. Vox Sang. 1987; 53:1–6) or by replacing the CM-Sephadex® by CM-Sepharose®-FF (Benny et al., J. Chromatogr. 1988; 433:363–366). Fuhge et al. (Transfus. Sci. 1990, 11:23S–33S) also report a process comprising two chromatographic steps on QAE- and phenyl-Sepharose® and a precipitation step with ammonium sulfate.

All these different processes include precipitation steps that must be followed by centrifugation; these processes have a poor selectivity, are difficult to carry out on large scale and give low yields.

DETAILED DESCRIPTION OF THE INVENTION

In order to by-pass these difficulties, the Applicant has succeeded in developing a process that does not involve any precipitation step or batch adsorption, but only column chromatographies.

Moreover, the Applicant has tested different types of chromatography gels and has chosen unconventional "tentacular" type ion exchanger gels, which separation capacity on C1-INH was proven particularly performant by the Applicant.

The tentacular ion exchanger gels are described by M üller (J. Chromatography, 1990; 510:133–140). They are distributed by Merck (Darmstadt-Germany) under the trade mark Fractogel-EMD® preceded by the abreviation of the ion exchanger grouping (TMAE-, DEAE-, DMAE-, $SO_3$-, COO-). They are composed of an inert, porous and semi-rigid Fractogel® type matrix, that is constituted of an oligoethyleneglyool glycidylmethacrylate and pentaerythritol-dimethacrylate copolymer, on which are grafted tentacles constituted of linear vinyl polymer chains (linear and not crosslinked as in traditional gels). The ion exchange groupings carried by these linear chains have a much geater mobility and are more independent of the matrix than those in traditional reticulated configurations. These properties justify the denomination of gels with mobile arms or tentacles.

Thus, the process of the present invention comprises two separation steps on chromatographic columns with tentacular type ion exchange gels, the first one on a weak anion exchanger gel, the second one on a strong cation exchanger gel.

The weak anion exchanger is a DMAE-type exchanger, the vinyl polymer grafted on the matrix being constituted of monomers of formula $CH_2=CHCONH(CH_2)_2N(CH_3)_2$.

The strong cation exchanger is a $SO_3^-$ grouping, the vinyl polymer grafted on the matrix being constituted of monomers of formula $CH_2=CHCONHC(CH_3)_2N(CH_2)SO_3^-$.

To carry out the process of the invention, one uses as a starting material a human plasma fraction free of cryoprecipitate and pre-purified by adsorption on a gel grafted on DEAE- groupings of DEAE-Sephadex® type, which eliminates the vitamin K-dependent proteins, then antithrombin III is eliminated by using an affinity chromatography on immobilized heparin.

Thus, the process does not interfere with the fractionation and the preparation of other blood factors of therapeutic interest.

The process of the invention comprises the following steps:

loading the prepurified plasma fraction on the first chromatographic column, chromatographic separation on the weak anion exchanger gel and elimination of the filtrate containing albumin, IgG, IgA, α.AT and α$_2$-macroglobulin, IgG, IgA, α.AT and α$_2$-macroglobulin, elution and elimination of the complement constituent C3, elution and recovery of the fraction containing the C1-INH, loading the eluate on the second chromatographic column, chromatographic separation on the strong cation exchanger gel and elimination of the filtrate and of a first fraction containing IgM, elution and recovery of C1-INH, concentration and freeze-drying of the eluate.

The first chromatographic separation is carried out in 20 mM sodium phosphate buffer, pH 7, supplemented with 60 mM NaCl. Raising the NaCl concentration of the buffer to 120 mM enables the elution of undesirable proteins, particularly the complement constituent C3; then, raising NaCl concentration to 170 mM enables the elution of C1-INH.

The second chromatographic separation is carried out in 20 mM sodium phosphate buffer, pH 7, supplemented with 30 mM NaCl and the C1-INH elution is obtained by raising the NaCl concentration of the buffer to 90 mM. A first minor fraction, containing the IgM, is eluted under the same conditions and is discarded; the major fraction containing the C1-INH comes out the column as a fraction neatly separated from the first one.

The process of the invention also comprises, preferably, 2 viral inactivation treatments. The first treatment, using a solvent/detergent, is applied to the eluate of the first chromatography so that the solvent/detergent is eliminated in the filtrate of the second chromatography. The second treatment is a sequential nanofiltration on filters of 35 nm then 15 nm, that is intended to eliminate possible small size viral contaminants. This treatment is carried out on the concentrated eluate of the second chromatography.

The invention also covers the C1-INH concentrate showing a specific activity of at least 6 U/mg protein, corresponding to a degree of purity higher than 85%. Its degree of purity, biochemical characteristics and biological activity make it entirely acceptable for therapeutical use, not only to compensate the above described deficiencies in C1-INH but also to treat various pathologies where inflammatory reactions are catalyzed by kallikrein and activated Hageman factor.

The following examples illustrate the invention, without limiting its scope.

EXAMPLE 1

Purification of C1-INH

A human plasma fraction free of cryoprecipitate is submitted to a two-step pre-purification by adsorption on DEAE-Sephadex®A50 (Pharmacia-LKB) to eliminate the vitamin K-dependent proteins and by affinity chromatography on heparin-Sepharose® (Pharmacia-LKB) to eliminate antithrombin-III.

The filtrate of the chromatography on heparin-Sepharose contains 50–70% of C1-INH normal concentration in plasma that averages 0.24 g/l.

The purification steps are performed at room temperature, on batches of 180 liters each of prepurified fractions.

After dialysis in a 10K ultrafiltration system (Filtron®) against the chromatography equilibration buffer, the plasma fraction is submitted to an anion exchange chromatography. The plasma fraction is loaded on a chromatographic column Moduline® P 630–250 (Amicon) packed with DMAE-Fractogel EMD® 650M (Merck) equilibrated with 20 mM sodium phosphate buffer, pH 7, supplemented with 60 mM NaCl.

The gel is washed with the equilibration buffer until the absorbance of the filtrate falls to the baseline. The filtrate of this chromatography contains baseline. The filtrate of this chromatography contains albumin, IgG, IgA, α-AT and α$_2$-macroglobulin, that are recycled into the fractionation circuit. Then the buffer is supplemented with NaCl to a concentration of 120 nM to remove undesirable proteins, particularly the complement constituent C3.

Then the C1-INH is eluted by raising the NaCl concentration of the buffer to 170 mM.

IgM, ceruloplasmin and complement constituent C4 remain strongly adsorbed to the column.

The eluate shows a specific activity of 1.3±0.2 U C1-INH/ mg protein corresponding to a purity of about 30%. The eluate is concentrated to 10 g proteins/l and dialyzed (on Filtron® 10K cassettes) against the equilibration buffer of the following chromatography ($SO_3$-Fractogel).

The eluate is submitted to a vital inactivation treatment with solvent/detergent, by mixing with TnBP 0.3% and Tween 80 1% (final concentrations) and by incubating at 25° C. for 7 hours, under gentle stirring.

Then the solution is submitted to a cation exchange chromatography on $SO_3$-Fractogel EMD®.

The solution treated with solvent/detergent is loaded on a Bioprocess® 252 column (Pharmacia) packed with $SO_3$-Fractogel EMD® 650(M) (Merck) equilibrated with 20 mM sodium phosphate buffer, pH ,7, supplemented with 30 mM NaCl.

The gel is washed with at least 12 times the column volume to remove the viral inactivation agents.

The C1-INH is then eluted by raising the concentration of NaCl of the buffer to 90 mM.

A first fraction containing essentially IgM is discarded. The main fraction containing C1-INH then elutes, clearly separated from the first one and it is collected. It shows a specific activity of 6.5±0.5 U/mg of protein corresponding to a purity of 84 to 92%.

The purified product recovery rate is of 40 to 50% from the starting fraction and of 25 to 30% from total plasma.

The eluate is then concentrated and dialyzed (on Filtron® 30K cassettes) in 10 mM trisodium citrate buffer at pH 7, supplemented with 150 mM NaCl.

Both column types are regenerated by means of subsequent washing with 1M NaCl, 1M sodium hydroxyde and 2M NaCl.

The concentrated eluate (1.2 liter at about 10 g/l of C1-INH antigen) is submitted to a second viral elimination treatment by sequential nanofiltration on filters with a porosity of 35 nm, then of 15 nm (Asahi BMM). The efficiency of this treatment for removal of small size marker viruses, such as poliomyelitis virus and bovine parvovirus, has already been demonstrated.

The concentrate is then dispensed in vials (5 ml/vial) and freeze-dried.

EXAMPLE 2

Analysis of the final product

C1-INH activity is measured as the capability to inhibit the C1-esterase by a chromogenic substrate (Berichrom®). One unit (UI) of C1-INH activity is defined as the activity present in 1 ml of normal plasma.

The freeze-dried final product is instantaneously (<1 minute) reconstituted in solution in ready-to-inject water; the solution is clear, colorless and stable during 24 hours at room temperature.

The characteristics of the final product are indicated in the following table

| Total proteins, g/l | 10.5 ± 1.5 |
| C1-INH-antigen, g/l | 9 ± 2 |
| C1-INH-activity, U/ml | 70 ± 10 |
| Specific activity, U/mg protein | 6.5 ± 0.5 |
| C3, g/l | 0.59 ± 0.29 |
| C4, g/l | <0.006 |
| IgG, g/l | 0.041 ± 0.004 |
| IgA, g/l | 0.056 ± 0.006 |
| IgM, g/l | 0.14 ± 0.03 |
| Albumin, g/l | 0–0.03 |
| Fibrinogen, g/l | 0.017 ± 0.005 |
| Ceruloplasmin, g/l | <0.015 |
| Tween 80, ppm | <10 |
| TnBP, ppm | 0.2 |

The ratio between the C1-INH activity and the quantity of C1-INH-antigen expressed in U/ml, is of 1.7 to 2, showing that the inhibitor remains stable all along the purification process.

The main contaminant is the complement constituent C3 representing 4 to 10% of total proteins.

Animal studies show that the product is apyrogenic and does not show any toxicity in mouse (tolerated dose is higher than 2 000 U/kg of corporal weight of the mouse). Intravenous injection to rats, with doses up to 300 U/kg of corporal weight, does not induce either hypotension or modification of cardiac rhythm.

I claim:

1. A process for preparing a C1-esterase inhibitor (C1-INH) concentrate, for therapeutic use, wherein the starting material is a human plasma fraction free of cryoprecipitate and pre-purified by adsorption on a gel with grafted diethylaminoethyl (DEAE)-groupings, then by affinity chromatography on immobilized heparin, said process comprising:

subjecting said human plasma fraction free of cryoprecipitate to a first separation step on a weak anion exchanger gel to obtain a first eluate;

subjecting said first eluate to a second separation step on a strong cation exchanger gel; and recovering said C1-INH concentrate, wherein said process does not employ any precipitation step.

2. The process according to claim 1, wherein the gels comprise an inert porous matrix, of a copolymer of oligoethyleneglycol, glycidylmethacrylate and pentaerythritol-dimethacrylate type with grafted non-crosslinked linear vinyl polymers carrying ionic groupings.

3. The process according to claims 1 or 2, wherein the weak anion exchanger is of dimethylaminoethyl (DMAE)-type.

4. The process according to claim 3, wherein the strong cation exchanger is concentration and freeze-drying of the eluate.

5. The process according to claims 1 or 2, wherein the weak anion exchanger is dimethylaminoethyl (DMAE).

6. The process according to claim 1, wherein the second chromatographic separation is carried out in 20 mM sodium phosphate buffer, pH 7, supplemented with 30 mM NaCl and the elution of C1-INH is obtained by raising the concentrations of NaCl of the buffer to 90 mM.

7. The process according to claim 1, wherein the eluate of the first chromatography is submitted to a viral inactivation treatment with a solvent and a detergent.

8. The process according to claim 1, which further comprises a step of elimination of possible small size viral contaminants by nanofiltration of the concentrated eluate of the second chromatography.

9. The process according to claim 1, wherein the first chromatographic separation is carried out in 20 mM sodium phosphate buffer, pH 7, supplemented with 60 mM NaCl and the elution of the C3 is obtained by raising the NaCl concentration of the buffer to 120 mM and that of C1-INH, by raising the NaCl concentration of the buffer to 170 mM.

10. A process for preparing a C1-esterase inhibitor (C1-INH) concentrate, for therapeutic use, comprising:

loading a prepurified plasma fraction on a first chromatographic column, said prepurified plasma fraction being obtained by subjecting a human plasma fraction free of cryoprecipitate to prepurification by adsorption on a gel with grafted diethylaminoethyl (DEAE)-groupings, followed by affinity chromatography on immobilized heparin;

performing a chromatographic separation on a weak anion exchanger gel of dimethylaminoethyl (DMAE)-type, and discarding the filtrate;

eluting and discarding the complement component C3;

eluting and recovering C1-INH;

loading the eluate on a second chromatographic column;

performing a chromatographic separation on a strong cation exchanger gel of a $SO_3$-grouping and discarding of the filtrate of a first fraction containing IgM;

eluting and recovering C1-INH;

concentrating and freeze-drying the eluate, wherein said process does not employ any precipitation step.

11. The process according to claim 10, wherein the first chromatographic separation is carried out in 20 mM sodium phosphate buffer, pH 7, supplemented with 60 mM NaCl and the elution of the C3 is obtained by raising the NaCl concentration of the buffer to 120 mM and that of C1-INH, by raising the NaCl concentration of the buffer to 170 mM.

12. The process according to claim 10, wherein the second chromatographic separation is carried out in 20 mM sodium phosphate buffer, pH 7, supplemented with 30 mM NaCl and the elution of C1-INH is obtained by raising the concentrations of NaCl of the buffer to 90 mM.

13. The process according to any one of claims 10 to 12, wherein the eluate of the first chromatography is submitted to a viral inactivation treatment with a solvent and a detergent.

14. The process according to claim 3, which further comprises a step of elimination of possible small size viral contaminants by nanofiltration of the concentrated eluate of the second chromatography.

15. A process for preparing a C1-esterase inhibitor (C1-INH) concentrate, for therapeutic use, comprising:

loading a prepurified plasma fraction on a first chromatographic column, said prepurified plasma fraction being obtained by subjecting a human plasma fraction free of cryoprecipitate to prepurification by adsorption on a gel with grafted diethylaminoethyl (DEAE)-groupings, followed by affinity chromatography on immobilized heparin;

performing a chromatographic separation on a weak anion exchanger gel of dimethylaminoethyl (DMAE), and discarding the filtrate, wherein said separation on a weak anion exchanger gel is carried out in 20 mM sodium phosphate buffer, pH 7, supplemented with 60 mM NaCl;

eluting and discarding the complement component C3, wherein said eluting of the complement component C3 is effected by raising the NaCl concentration of the buffer to 120 mM;

eluting and recovering C1-INH, wherein the elution of C1-INH is obtained by raising the NaCl concentration of the buffer to 170 mM, and wherein said step of eluting and recovering said C1-INH follows said step of eluting and discarding said complement component C3;

loading the eluate on a second chromatographic column;

performing a chromatographic separation on a strong cation exchanger gel of a $So_3$-grouping and discarding of the filtrate of a first fraction containing IgM, wherein said chromatographic separation on a strong cation exchanger gel is carried out in 20 mM sodium phosphate buffer, pH 7, supplemented with 30 mM NaCl;

eluting and recovering C1-INH, wherein the elution of C1-INH is obtained by raising the NaCl concentration of the buffer to 90 mM;

concentrating the eluate, wherein said process does not employ any precipitation step.

16. A process for preparing a C1-esterase inhibitor (C1-INH) concentrate, for therapeutic use, comprising:

loading a prepurified plasma fraction on a first chromatographic column, said prepurified plasma fraction being obtained by subjecting a human plasma fraction free of cryoprecipitate to prepurification by adsorption on a gel with grafted diethylaminoethyl (DEAE)-groupings, followed by affinity chromatography on immobilized heparin;

performing a chromatographic separation on a weak anion exchanger gel of dimethylaminoethyl (DMAE), and discarding the filtrate;

eluting and discarding the complement component C3;

eluting and recovering C1-INH;

loading the eluate on a second chromatographic column;

performing a chromatographic separation on a strong cation exchanger gel of a $SO_3$-grouping and discarding of the filtrate of a first fraction containing IgM;

eluting and recovering C1-INH;

concentrating and freeze-drying the eluate, wherein said process does not employ any precipitation step.

17. The process according to claim 16, wherein the first chromatographic separation is carried out in 20 mM sodium phosphate buffer, pH 7, supplemented with 60 mM NaCl and the elution of the C3 is obtained by raising the NaCl concentration of the buffer to 120 mM and that of C1-INH, by raising the NaCl concentration of the buffer to 170 mM.

18. The process according to claim 16, wherein the second chromatographic separation is carried out in 20 mM sodium phosphate buffer, pH 7, supplemented with 30 mM NaCl and the elution of C1-INH is obtained by raising the concentrations of NaCl of the buffer to 90 mM.

19. The process according to any one of claims 16 to 18, wherein the eluate of the first chromatography is submitted to a viral inactivation treatment with a solvent and a detergent.

20. The process according to claim 19, which further comprises a step of elimination of possible small size viral contaminants by nanofiltration of the concentrated eluate of the second chromatography.

21. A C1-INH concentrate for therapeutic use obtained by the process according to any one of claims 1, 10, 15, and 16, having a specific activity at least equal to 6 U/mg of protein corresponding to a purity higher than 85%.

* * * * *